United States Patent [19]

Funk

[11] Patent Number: 5,037,193

[45] Date of Patent: Aug. 6, 1991

[54] BIFOCAL SEGMENT DEMONSTRATION AND MEASURING APPARATUS

[76] Inventor: William F. Funk, 1315 Sugar Crossing, Sugarland, Tex. 77478

[21] Appl. No.: 522,665

[22] Filed: May 11, 1990

[51] Int. Cl.$^5$ .............................................. A61B 3/10
[52] U.S. Cl. ...................................... 351/204; 33/200
[58] Field of Search .................. 351/204, 158; 33/200, 33/507

[56] References Cited

U.S. PATENT DOCUMENTS

| | | | |
|---|---|---|---|
| 2,632,257 | 3/1953 | Belgard | 351/204 |
| 4,575,946 | 3/1986 | Bommarito | 33/200 |
| 4,653,192 | 3/1987 | Conrad et al. | 351/204 |

*Primary Examiner*—Paul M. Dzierzynski
*Attorney, Agent, or Firm*—Geoffrey A. Mantooth

[57] ABSTRACT

The apparatus has a support portion and a holder portion. The support portion includes a stick with two ends. A bifocal segment is coupled to one end of the stick. The holder portion has side walls that clamp onto the eye wire of an eyeglass frame. The holder portion also has arms that clamp the stick to the holder portion. The arms allow the stick and the bifocal segment to move up and down. An eyeglass wearer can install the holder portion onto one of the lower eye wires of the frame, don the frame, and adjust the position of the bifocal segment to a satisfactory position. The bifocal segment position is then measured with the stick. The measurement is used to manufacture the corrective lenses for the frame.

17 Claims, 2 Drawing Sheets

BIFOCAL SEGMENT DEMONSTRATION AND MEASURING APPARATUS

FIELD OF THE INVENTION

The present invention relates to eyewear, and in particular to eyeglasses that are used to correct vision.

BACKGROUND OF THE INVENTION

Bifocal eyewear provides two corrective lens of difference focal lengths for each eye. Typically, the primary corrective lens is on top of and is much larger than the secondary corrective lens. The secondary corrective lens, or bifocal segment, is located at the bottom and is typically used for reading or other close-up work.

The location and size of the bifocal segments can be varied to suit the individual needs and comfort of the wearer. In the prior art, the position of the bifocal segments is determined by measurement with a ruler or pupillary distance (p.d.) stick. To make a measurement, the wearer dons the prospective eyewear frame and a skilled assistant measures the distance from the lowest part of the frame to the lower eyelid with the p.d. stick. This measurement determines the location of the bifocal segment in the eyewear frame. Another prior art device uses a ruler fixedly coupled to the inside of a frame, in place of the lens. The measurement is read off of the fixed ruler.

Unfortunately, the prior art system of positioning the bifocal segment ignores the individual needs and comfort of the wearer. The wearer is unable to try out the positions of the bifocal segments. As such, the bifocal segment is often located in an uncomfortable position. Furthermore, the wearer is frequently unaware of the problem until the eyewear has been returned to the wearer already fitted with the corrective lenses, and the wearer tries them on for the first time. At this time, it is too late to adjust the location of the bifocal segments because the corrective lens have already been manufactured for the frame.

What is needed is an apparatus wherein a wearer can try out the position of bifocal segments in eyeglass frames before the lenses are manufactured.

SUMMARY OF THE INVENTION

It is an object of the present invention to provide an apparatus that will permit an eyeglass wearer to test the position of bifocal segments before the manufacturing and installation of the segments.

It is a further object of the present invention to provide an apparatus that will enable the measurement of the position of bifocal segments relative to eyeglass frames.

The apparatus of the present invention includes support means and holder means. The support means has two ends, with one of the ends being coupled to a bifocal segment means. The holder means is for coupling the support means to the eyewear. The holder means has clamp means that is adapted for removably coupling the holder means to the eyewear. The holder means has retaining means for receiving and retaining the support means to the holder means. The retaining means allows the support means to slide relative to the holder means such that the bifocal segment means can move relative to the eyewear when the holder means is coupled to the eyewear, wherein a wearer of said eyewear can test the position of the bifocal segment means in the eyewear.

In one aspect, the support means has lines thereon, which lines allow the measurement of the position of the bifocal segment means with respect to the eyewear.

In another aspect, the clamp means provides first and second flexible side walls that are connected together so as to form a channel. The channel has an opening which is adapted for receiving a portion of the eyewear. The first and second side walls flex apart so as to receive a portion of the eyewear into the channel.

In still another aspect, the holder means has two ends, with one of the ends being rounded so as to conform with the rounded shape of the eyewear, wherein the apparatus can be coupled to the eyewear and worn in such a way that it will not interfere with the nose of a wearer.

In still another aspect, the retaining means comprises flexible arms that project out from the holder means. The arms flex so as to expand outwardly so that the support means can be received therein.

With the apparatus of the present invention, a prospective wearer of a pair of eyeglasses can try out various positions of the bifocal segments to find out the most satisfactory position. The apparatus is quickly installed onto an eyeglass frame. The apparatus is also used to measure the location of the bifocal segments.

DESCRIPTION OF PREFERRED EMBODIMENT

Figure 1:
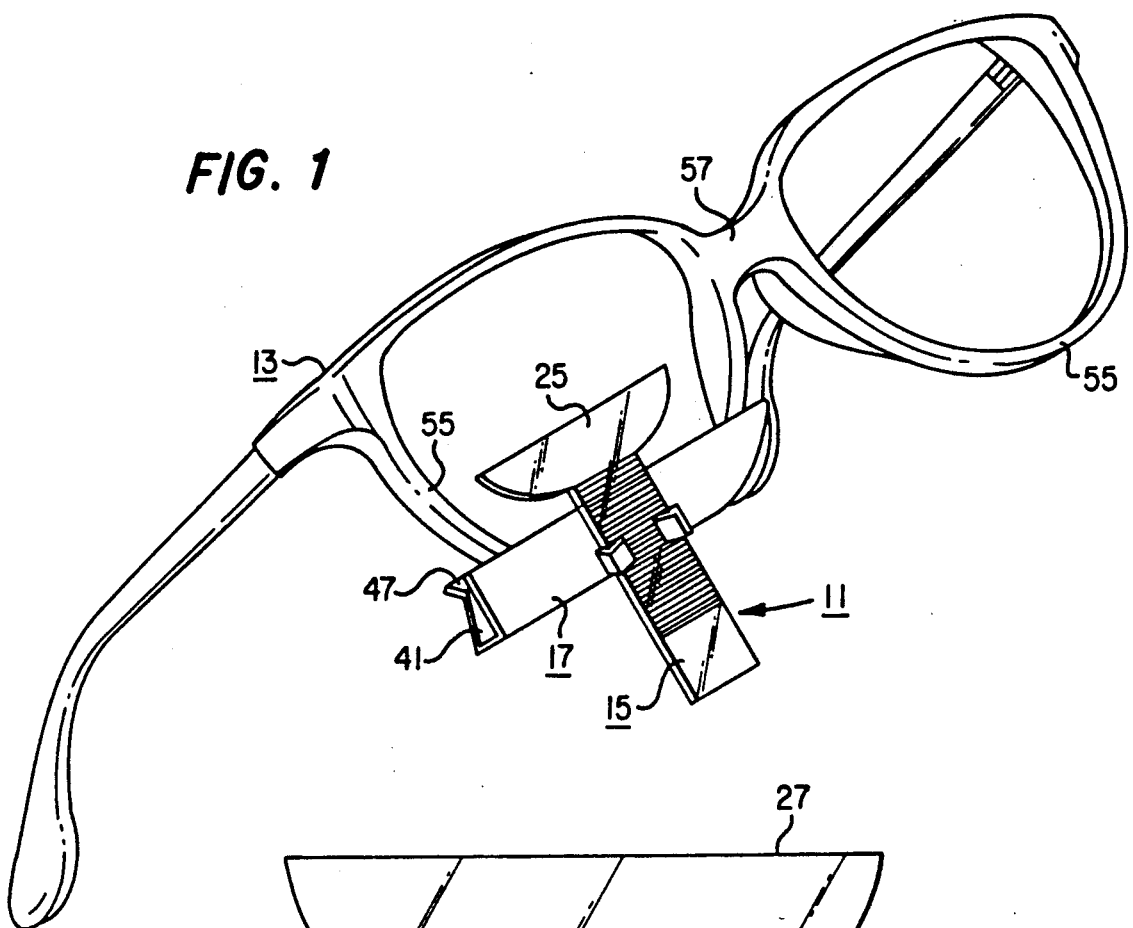
FIG. 1 is an isometric view of the apparatus of the present invention, in accordance with a preferred embodiment, shown installed on an eyewear frame.

In FIG. 1, there is shown an isometric view of the apparatus 11 of the present invention, in accordance with a preferred embodiment. The apparatus 11, which is shown attached to an eyeglass frame 13, is used to demonstrate the position of bifocal segments to a prospective wearer of the eyeglass frame. By using the apparatus, the prospective wearer can adjust the position of the bifocal segment to his satisfaction. Once the bifocal segment is satisfactorily positioned, the apparatus is used to measure the position of the bifocal segment, wherein the lenses for the eyeglass frame can be manufactured.

The apparatus 11 includes a support portion 15 and a holder portion 17.

Figure 2:
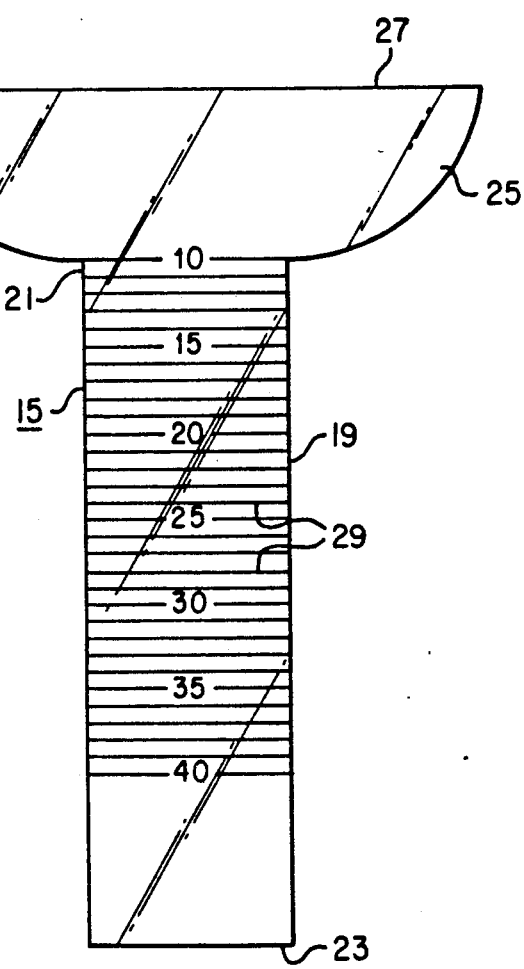
FIG. 2 is a plan view of the support portion and its associated bifocal segment.
Figure 3:
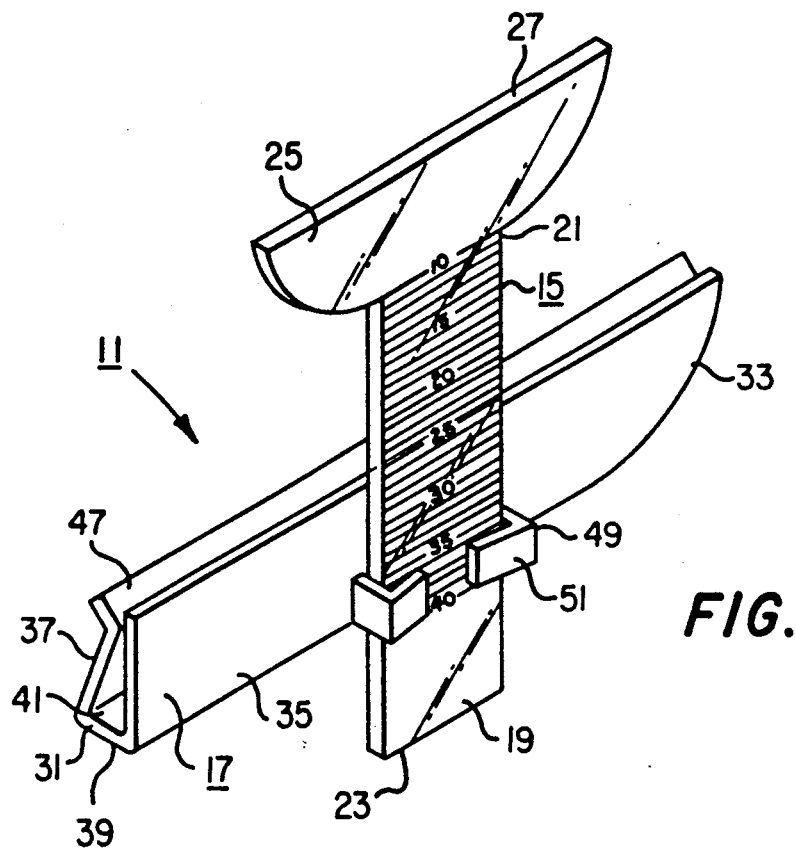
FIG. 3 is an isometric view of the apparatus.

Referring to FIGS. 2 and 3, the support portion 15 is flat and includes a measuring stick 19. The stick has upper and lower ends 21, 23 and is rectangular in shape. A bifocal segment 25 is coupled in an integral manner to the upper end 21 of the stick 19. The bifocal segment 25 has a straight upper edge 27 that mimics the straight upper interface line between the two corrective lenses in one eye wire of a pair of bifocal eyeglasses. The size and shape of the bifocal segment 25 may mimic the size and shape of the actual corrective bifocal segment which is to be inserted into the eyeglass frame. The stick 19 has lines 29 extending parallel to the upper edge 27 of the bifocal segment 25. The lines 29 are used for measuring distances from the bifocal segment upper edge 27. In accordance with conventional practice in fitting bifocal segments, the lines are spaced one millimeter apart.

Every tenth millimeter is so marked with a number for ease of measurement. The lines may be marked on the stick or etched into the stick surface. The bifocal segment 25 is unlined, for ease of viewing therethrough.

Figure 4:
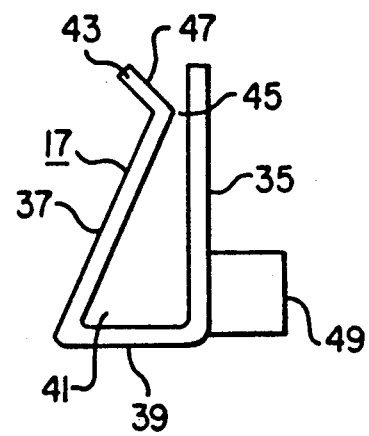
FIG. 4 is an end view of the holder portion.

Referring to FIGS. 3 and 4, the holder portion 19 has first and second ends 31, 33 and front and back side walls 35, 37 extending between the ends. The lower edge of the front side wall 35 is coupled to a bottom wall 39. The bottom wall 39 extends perpendicularly from the front side wall 35 in a rearward direction. The lower edge of the back side wall 37 is coupled to the rearward edge of the bottom wall 37 such that a channel 41 is formed between the front and back side walls 35, 37. The back side wall 37 is inclined toward the front side wall 35 so that the upper end portion 43 of the back side wall 37 is separated from the front side wall 35 by a narrow gap 45. The upper end portion 43 of the back side wall 35 is bent rearwardly away from the front side wall so as to provide a beveled surface 47. The beveled surface 47 provides for ease of insertion of the holder portion onto an eyeglass frame.

The second end 33 of the holder portion 17 is rounded, as shown in FIG. 1, so as to avoid projecting too far beyond the lower portion of the eye wire 55 and interferring with the nose of the wearer.

Figure 5:
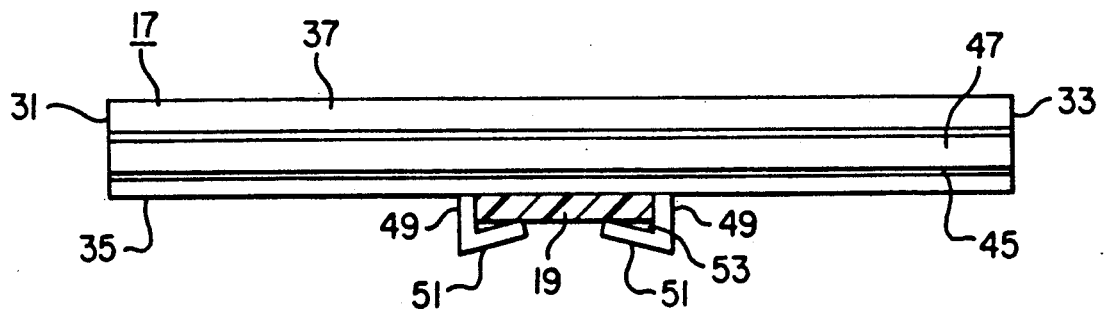
FIG. 5 is a top plan view of the holder portion, showing the measuring stick in cross-section.

The front side wall 35 of the holder portion 17 has two arms 49 for receiving the stick 19 (see FIGS. 3-5). The arms 49 project outwardly from the front side wall 35 in a forward direction. The arms, which are generally L-shaped when viewed from above as shown in FIG. 5, have their free ends 51 inclined inwardly toward the front wall 35. There is a gap 53 between the front side wall 35 and the free ends 51 of the arms, which gap is normally smaller than the thickness of the stick 19. The free ends 51 of the arms can flex outwardly to increase the size of the gap 53 so as to receive the stick 19. The arms 49 are preferably located close to the bottom wall 39 so as to allow the bifocal segment 25 to be positioned close to the bottom wall 39. This enables the bifocal segment to be positioned as low as possible relative to the eye wire 55 when the apparatus 11 is installed on an eyeglass frame.

In the preferred embodiment, the support portion 15 and the holder portion 17 are made of plastic. The bifocal segment 25 is transparent so as to allow viewing therethrough when worn on eyeglass frames. The bifocal segment 25 can have little or no correction to it or it can be formed so as to be a corrective lens in order to provide more realistic mimicry of an actual corrective bifocal segment. The holder portion 17 is made out of flexible plastic so that the front and back side walls 35, 37 can flex for installation and removal from an eyeglass frame and so that the arms 49 can flex in and out.

The use of the apparatus 11 will now be described. The apparatus 11 is assembled together by inserting the stick 19 into the gap 53 formed between the arms 49 and the front side wall 35. The stick 19 is oriented as shown in FIG. 3, wherein the bifocal segment 25 is located by the upper edges of the front and back side walls. The free ends 51 of the arms 49 are pulled away from the front side wall 35 to allow insertion of the stick. The arms are released, wherein the stick 19 is clamped in place between the free ends 51 of the arms 49 and the front side wall 35. The stick, however, is able to slide up and down. The stick 19 is used to support the bifocal segment 25 and to measure its position.

The apparatus 11 is installed on the lower portion of one of the eye wires 55. The eye wire 55 is that portion of an eyeglass frame 13 that encircles the lens. There are two eye wires, one for each eye. When the eyeglass frame 13 is worn to position the bifocal segments, there are no corrective lens installed in the eye wires. The holder portion 17 is inserted onto the lower portion of an eye wire by inserting the eye wire 55 into the channel 41 by way of the gap 45. As the eye wire 55 is inserted into the holder portion, it is guided into the gap 45 by the beveled surface 47. As the eye wire 55 passes through the gap 45, the front and back side walls 35, 37 flex apart and then towards each other. The front and back side walls 35, 37 clamp the holder portion 17 to the eye wire 55. The holder portion is oriented so that the stick 19 is in front of the eye wire, wherein the eye wire is interposed between a wearer's eye and the stick. The second end 33 of the holder portion is located in proximity to the nose bridge 57.

Once the apparatus 11 has been installed onto the frame, the wearer dons the eyeglass frame 13 to check the position of the bifocal segment. The wearer can adjust the height of the bifocal segment 25 by sliding the stick 19 up and down within the arms 49. The wearer can also adjust the horizontal location of the bifocal segment for demonstration purposes by sliding the holder portion 17 along the eye wire 55 towards his nose or away from his nose. With the apparatus 11 of the present invention, the wearer can walk around the room, looking through the bifocal segment 25 and adjusting its position to his or her satisfaction. Once the bifocal segment has been satisfactorily positioned, the position of the bifocal segment 25 is measured. The lines 29 and the stick 19 are used to measure from the upper edge 27 of the bifocal segment to the bottom of the eye wire 55. The holder portion may be made of transparent plastic to aid in this measurement. After the measurement has been taken, the holder portion is easily removed from the eye wire. The measurement is then used to manufacture the lenses for the eyeglass frame 13.

The apparatus of the present invention can be provided in pairs; one for the right eye wire as shown in FIG. 1, and one for the left eye wire. Both apparatuses have rounded ends to avoid interference with the wearer's nose.

Some eyeglass frames do not have a lower eye wire portion, in order to reduce the weight of the frame. For these types of frames, a sample frame with an uncorrective or plano lens is used. The holder portion is inserted onto the lower edge of the lens.

Although the apparatus has been described with measuring lines on the stick 19, a separate measuring ruler can be used to measure the position of the bifocal segment.

The foregoing disclosure and the showings made in the drawings are merely illustrative of the principles of this invention and are not to be interpreted in a limiting sense.

I claim:
1. An apparatus for use with eyewear, comprising:
   a) support means having two ends, said support means having a bifocal segment means coupled to one end;
   b) holder means for coupling said support means to said eyewear, said holder means having clamp means, said clamp means being adapted for removably coupling said holder means to said eyewear, said holder means having retaining means for receiving and retaining said support means to said holder means, said retaining means allowing said support means to slide relative to said holder means such that said bifocal segment means can move relative to said eyewear when said holder means is coupled to said eyewear, wherein a wearer of said eyewear can test the position of said bifocal segment means in said eyewear.

2. The apparatus of claim 1 wherein said support means has lines thereon, which lines allow measurement of the position of said bifocal segment means with respect to said eyewear.

3. The apparatus of claim 2 wherein said clamp means comprises first and second flexible side walls connected together so as to form a channel, said channel having an opening which is adapted for receiving a portion of said eyewear, said first and second side walls flexing apart so as to receive a portion of said eyewear into said channel, said first and second side walls being adapted for clamping onto said eyewear.

4. The apparatus of claim 3 wherein said holder means has two ends, one of said holder means ends being rounded so as to conform with the rounded shape of said eyewear, wherein said apparatus can be coupled to said eyewear and worn in such a way so that it would not interfere with the nose of said wearer.

5. The apparatus of claim 1 wherein said holder means has two ends, one of said holder means ends being rounded so as to conform with the rounded shape of said eyewear, wherein said apparatus can be coupled to said eyewear and worn in such a way so that it would not interfere with the nose of said wearer.

6. The apparatus of claim 1 wherein said clamp means comprises first and second flexible side walls connected together so as to form a channel, said channel having an opening which is adapted for receiving a portion of said eyewear, said first and second side walls flexing apart so as to receive a portion of said eyewear into said channel, said first and second side walls being adapted for clamping onto said eyewear.

7. An apparatus for use with eyewear, comprising:
a) support means comprising a stick having two ends, said stick having bifocal segment means coupled to one end;
b) holder means adapted for coupling onto said eyewear, said holder means having two ends with first and second flexible side walls extending between said holder means ends, said first and second side walls being connected together so as to form a channel, said channel having an opening which is adapted for receiving a portion of said eyewear, said first and second side walls flexing apart so as to receive a portion of said eyewear into said channel, said first and second side walls being adapted for clamping onto said eyewear;
c) said holder means having retaining means for retaining said stick to said holder means, said retaining means comprising flexible arms projecting out from one of said first and second side walls, said arms being separated from said respective side wall by a gap, said arms flexing so as to expand said gap so that said stick can be received by said gap, said stick being slidable with respect to said holder means, said arms releasably retaining said stick in position relative to said holder means.

8. An apparatus for use with eyewear, comprising:
a) bifocal segment means for mimicking a corrective bifocal segment lens;
b) extension means having two ends, with one of said ends being coupled to said bifocal segment means such that said extension means extends from said bifocal segment means;
c) clamp means for removably clamping onto an eyeglass frame, said clamp means having retaining means located thereon, said retaining means for retaining said extension means to said clamp means, said retaining means allowing said extension means to move relative to said clamp means, wherein the position of said bifocal segment means can be adjusted.

9. The apparatus of claim 8, wherein said bifocal segment means comprises a straight upper edge which mimics an interface line between corrective lenses in bifocal eyeglasses.

10. The apparatus of claim 9 wherein said clamp means is adapted to clamp onto an eyeglass frame such that said clamp means can move along said frame to adjust the position of said bifocal segment means closer to or away from a nose bridge of said frame.

11. The apparatus of claim 8 wherein said clamp means is adapted to clamp onto an eyeglass frame such that said clamp means can move along said frame to adjust the position of said bifocal segment means closer to or away from a nose bridge of said frame.

12. The apparatus of claim 8 wherein said retaining means comprises arms that project out from said clamp means, said arms being generally "L" shaped and clamping said extension means between said arms and said clamp means.

13. The apparatus of claim 12 wherein said extension means comprises a flat ruler having markings thereon, said markings being for measuring the position of said bifocal segment means.

14. The apparatus of claim 13 wherein said clamp means comprises two clamping members that are separated from each other by a channel, said channel for receiving a portion of said eyewear, said clamping members being flexible so as to allow the expansion of said channel for the insertion of said eyewear portion.

15. The apparatus of claim 12 wherein said clamp means comprises two clamping members that are separated from each other by a channel, said channel for receiving a portion of said eyewear, said clamping members being flexible so as to allow the expansion of said channel for the insertion of said eyewear portion.

16. The apparatus of claim 8 wherein said clamp means comprises two clamping members that are separated from each other by a channel, said channel for receiving a portion of said eyewear, said clamping members being flexible so as to allow the expansion of said channel for the insertion of said eyewear portion.

17. The apparatus of claim 8 wherein said extension means comprises a flat ruler having markings thereon, said markings being for measuring the position of said bifocal segment means.

* * * * *